United States Patent [19]

Sawada et al.

[11] Patent Number: 5,326,597
[45] Date of Patent: Jul. 5, 1994

[54] METHOD OF PRODUCING OXYGEN SENSOR FOR AIR-FUEL RATIO CONTROL HAVING A PROTECTIVE LAYER INCLUDING OXYGEN STORAGE MATERIAL

[75] Inventors: Toshiki Sawada; Masaru Yamano; Kazuo Taguchi; Takao Kojima; Hiroyuki Ishiguro; Masahiko Yamada, all of Aichi, Japan

[73] Assignee: NGK Spark Plug Co., Ltd., Nagoya, Japan

[21] Appl. No.: 840,829

[22] Filed: Feb. 25, 1992

Related U.S. Application Data

[62] Division of Ser. No. 479,695, Feb. 14, 1990, Pat. No. 5,160,598.

[30] Foreign Application Priority Data

Feb. 14, 1989 [JP] Japan ..................... 1-32603
Feb. 14, 1989 [JP] Japan ..................... 1-32604
Feb. 14, 1989 [JP] Japan ..................... 1-32605

[51] Int. Cl.$^5$ .................. B05D 1/00; B05D 5/12; B05D 1/36; B05D 1/18
[52] U.S. Cl. .................. 427/448; 427/454; 427/126.3; 427/126.4; 427/226; 427/190; 427/205; 427/443.2
[58] Field of Search ............ 427/34, 126.3, 126.5, 427/126.4, 126.6, 226, 185, 190, 205, 423, 430.1, 443.2, 453, 454, 448

[56] References Cited

U.S. PATENT DOCUMENTS

| 4,199,425 | 4/1980 | Sinkevitch | 204/429 |
| 4,378,385 | 3/1983 | Hughes | 427/126.3 |
| 4,477,487 | 10/1984 | Kojima et al. | 204/429 |
| 4,536,241 | 8/1985 | Logothetis et al. | 427/126.3 |
| 4,584,086 | 4/1986 | Hayakawa et al. | 204/429 |
| 4,834,051 | 5/1989 | Tanaka et al. | 204/429 |
| 4,840,913 | 6/1989 | Logothetis et al. | 204/431 |
| 4,851,105 | 7/1989 | Ishiguro et al. | 204/429 |

Primary Examiner—Marianne Padgett
Attorney, Agent, or Firm—Fish & Richardson

[57] ABSTRACT

Oxygen sensor for air-fuel ratio control is provided with a sensor element having an oxygen ion-conductive main body and electrodes on both sides thereof, and at least one porous protective layer covering the electrode on the exhaust gas side. The protective layer includes an oxygen storage component OSC without copresence of a noble metal catalyst. The protective layer is intermeshingly connected to the main body via spherical protrusions of the main body. Double-layered protective layer structure includes OSC noncontaining layer (optionally containing catalyst) and OSC containing layer, as inner and outer protective layer or vice versa. OSC containing layer is formed by impregnation with OSC-solution through immersing the respective porous protective layer, or by cosintering the OSC containing green coating layer. By impregnation 0.2-8 wt %, or by cosintering 0.2-30 wt %, of OSC metal element is containable. The outer protective layer is thinner and more porous than the inner protective layer. Any of the protective layers can be formed by flame spraying.

40 Claims, 11 Drawing Sheets

FIG. 23(a)
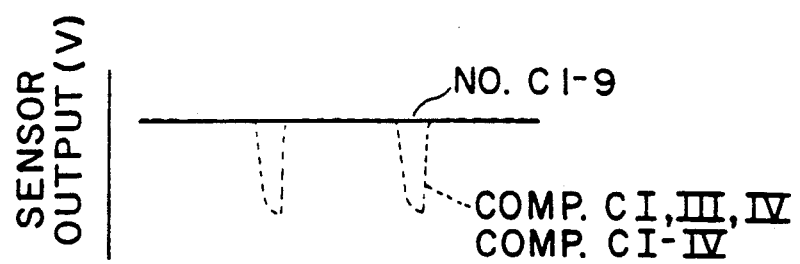
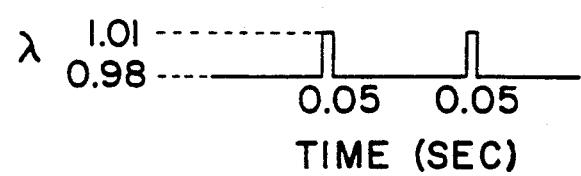
FIG. 23(b)

METHOD OF PRODUCING OXYGEN SENSOR FOR AIR-FUEL RATIO CONTROL HAVING A PROTECTIVE LAYER INCLUDING OXYGEN STORAGE MATERIAL

This application is a divisional application of U.S. application Ser. No. 07/479,695, filed Feb. 14, 1990, now U.S. Pat. No. 5,160,598 issued Nov. 3, 1992.

FIELD OF THE INVENTION

This invention relates to an oxygen sensor for air-fuel ratio control which is utilized in combination with a three way catalyst in an exhaust-gas purification system for automobiles and the like.

Particularly, the present invention relates to an oxygen sensor or air-fuel ratio control, provided with a sensor element having an oxygen ion-conductive main body and electrodes disposed on both the sides of the main body, and a protective layer at covering the electrode on a side assigned to be exposed to a gas to be measured (particularly exhaust gas).

BACKGROUND

The regulation of exhaust gas emissions from automobiles and the like has become more and more strict, and many oxygen sensors have been developed. Under such circumstances, there has been proposed also an oxygen sensor having a layer which includes a catalyst and cerium oxide or the like which have the function of occluding and releasing oxygen (JP Patent Kokai Publication Nos. 61-79155 (1986) and 62-245148 (1986)).

However, oxygen sensors are usually used under conditions of severe heat cycles, and in every oxygen sensor according to the above-described proposal, the layer including cerium oxide and the like and the catalyst peels from the sensor element during its use. Furthermore, cerium oxide and the like and the catalyst are mixedly coated so that, the both components exist in a single layer.

PROBLEMS IN THE ART

Accordingly, the function of occluding and releasing oxygen by cerium oxide and the like is excessively increased under the strong influence of the catalyst component, and the control frequency of the sensor is decreased and occasionally falls below the range of a three way catalyst in an exhaust-gas purification system.

Oxygen sensors for air-fuel ratio control are exposed to the exhaust gas containing poisoning substances such as Si, Ca, P, C and the like during use. Accordingly, compounds are produced through reaction of cerium oxide and the like with the poisoning substances, so that the oxygen occluding and releasing function is inhibited during a use. Particularly, a not negligible amounts of such compounds are produced during long-term use, thereby also promoting the peeling-off of the layer containing such cerium oxide and the like from the sensor element.

These problems are counted as disadvantages in the conventional art.

SUMMARY OF THE DISCLOSURE

Therefore, it is a primary object of the present invention to provide a novel oxygen sensor with improved properties over the conventional oxygen sensors having the disadvantages hereinabove mentioned.

Further objects will become apparent from the entire disclosure.

1st Aspect

According to the First Aspect of the present invention there is provided an oxygen sensor for air-fuel ratio control of the kind aforementioned wherein a protective layer made of a heat-resistant metal oxide is provided extending over at least an electrode on the side assigned to be exposed to the gas to be measured of the sensor element, the main body of the sensor element comprises a base portion and a portion with a plurality of spherical protrusions (referred to as a "spherically-protruded portion" hereinafter), the protective layer being intermeshingly connected to the base portion via the spherically-protruded portion, and the protective layer includes an oxygen storage component without substantial copresence of a noble metal catalyst.

According to this oxygen sensor of the First Aspect, the spherically-protruded portion functions, as it were, as a wedge, which can strongly connect together the main body of the sensor and the protective layer. Hence, even under the usual conditions of severe heat cycles, the protective layer securely protects the main body of the sensor element and the electrode from exhaust gases without deterioration in durability, such as peeling and the like. Consequently, it is possible to provide the function of the oxygen storage component, i.e., oxygen-occluding substance termed hereinafter "OSC") included within the protective layer for a long period of use. That is, the oxygen storage component included within the inventive protective layer has hardly any oxygen adsorption capability at the moment a fuel rich state that has an excess air ratio λ less than "1" is attained, and the oxygen adsorption capability increases at the moment a fuel lean state is attained that is an excess air ratio λ higher than "1" (see FIG. 7). Hence, the oxygen storage component first adsorbs oxygen when the amount of air rapidly increases at the moment of acceleration and the like (at the moment of the fuel lean state), and an exhaust gas having less oxygen than the usual exhaust gas reaches the sensor element, resulting in a retarded output timing of a lean signal by the sensor. When the engine has terminated acceleration and returns to a steady running state (like coasting), the protective layer for protecting the measuring electrode protects the sensor from deviation in λ-point and decrease in output.

Accordingly, the deviation in λ-point (the so-called rich excursion) due to rapid increase in the amount of air can be prevented as much as possible by the oxygen storage component, and it is therefore possible to achieve an exact air-fuel ratio control at the moment of acceleration as well as during and steady running during long-term use.

2nd Aspect

Next, according to the Second Aspect of the present invention there is provided a method of producing an oxygen sensor for air-fuel ratio control in which a protective layer is formed on the side of the sensor element assigned to be exposed to an exhaust gas having the following points:

applying to the element spherical substances made of the material of the main body of the sensor element at least at a corresponding to the position where an electrode exists, and immersing the element in a solution of a metal salt of an oxygen storage component after the formation of a coating layer of heat-resistant metal oxide.

According to this production method, the above-described oxygen sensor, that is, an oxygen sensor which securely protects the main body of the sensor element and the electrode from deterioration over a long period of use due to exhaust gases even under the usual conditions of severe heat cycles, and which can stably provide the function of the OSC, can be produced with an excellent mass-production capability.

3rd Aspect

According to the 3rd Aspect of the present invention, there is provided an oxygen sensor for air-fuel ratio control of the kind aforementioned at the introduction, wherein a first protective layer and a second protective layer, each made of a heat-resistant metal oxide, are provided on the side of the sensor element assigned to be exposed to the gas to be measured, the first protective layer being disposed closer to the electrode than the second, the first protective layer includes a noble metal catalyst, and the second protective layer includes an oxygen storage component without substantial copresence of the noble metal catalyst.

According to this Third Aspect, the 1st and 2nd protective layers contain the noble metal catalyst and the oxygen storage component, respectively, isolated from each other. Therefore the noble metal catalyst can fully carry out its catalytic function, and the oxygen storage component its oxygen occluding/releasing function, without adversely affecting each other. The noble metal catalyst contained in the first protective layer serves to equilibrize the unburnt components present in the exhaust gas. Thus, incidence of the undesirable deviation toward the lean side of air-fuel ratio (or excess air ratio $\lambda$) due to the unburnt components can be reduced, thereby ensuring exact control of the air-fuel ratio can be reduced as well as after a long period of use.

On the other hand, the oxygen storage component present in the 2nd protective layer has almost no oxygen-occluding ability at the fuel rich region i.e., a ratio less than the theoretical air-fuel ratio (=excess air ratio "1"), and exhibits an increased oxygen-occluding ability in the fuel lean region. This enables the OSC layer to momentarily or transiently occlude oxygen at the time of rapid air increase (fuel lean time) such as acceleation time, thereby allowing the exhaust gas having less oxygen than the usual exhaust gas to reach the sensor element itself (its main body), all resulting in a retarded output of the lean signal from the oxygen sensor. On the other hand, when the engine returns to the steady running state after terminating the acceleration, the 2nd protective layer acts to protect the measuring electrode as a protective layer cooperating with the 1st protective layer, yet more, and ensures prevention of the $\lambda$ point deviation and the output decrease through the dissipation of the noble metal catalyst in the 1st protective layer during use.

Accordingly, the 3rd Aspect can prevent: (a) the $\lambda$ point deviation due to unburnt components in the exhaust gas (deviation toward the fuel lean side) caused by the noble metal catalyst, as well as (b) the $\lambda$ point deviation due to the rapid air increase (so-called rich excursion) caused by the oxygen storage component, respectively. All of these characteristics permit exact air-fuel ratio control during any period of acceleration or during steady running states over long periods of time (long-term use).

4th Aspect

According to the 4th Aspect of the present invention there is provided a method of producing an oxygen sensor for air-fuel ratio control, particularly for forming a protective layer on a side of the sensor element assigned to be exposed to an exhaust gas, having the steps:

immersing in a solution of a metal salt of noble metal after formation of a first coating layer of heat-resistant metal oxide, and (4a) coating a slurry of heat-resistant metal oxide and oxygen storage component for forming a second protective layer;

or alternatively of step (4a) above, (4b) forming a 2nd protective layer of heat-resistant metal oxide followed by immersing in a solution of a metal salt of an oxygen storage component.

According the method of the 4th Aspect, the 2nd protective layer containing the oxygen storage component can be formed after the formation of the 1st protective layer containing the noble metal, thus ensuring the isolated incorporation of the noble metal and oxygen storage component in the separate 1st and 2nd protective layers, respectively. This method can provide mass production of the oxygen sensor of the 3rd Aspect, in which the noble metal and oxygen storage component can fully develop their respective functions, i.e., catalytic function for the noble metal and oxygen occluding function for the oxygen storage component without interfering with each other.

5th Aspect

Now under the 5th Aspect of the present invention, there is provided an oxygen sensor for air-fuel ratio control of the kind aforementioned, in which:

a first protective layer and a second protective layer, each made of a heat-resistant metal oxide, are provided on the side of the sensor element assigned to be exposed to the gas to be measured, the first protective layer being disposed closer to the electrode than the second protective layer, and the first protective layer includes an oxygen storage component without substantial copresence of a noble metal catalyst.

According to the 5th Aspect, the oxygen sensor includes the 1st and 2nd protective layers of heat-resistant metal oxide, in which the 1st protective layer disposed closer to the sensor element itself (or electrode disposed thereon) contains the oxygen storage component. The provision of the 2nd protective layer over the 1st protective layer ensures that the oxygen storage component contained in the 1st protective layer can develop its oxygen-occluding/releasing function in a stable state for a long period of time without being poisoned by the elements Si, Ca, P, C, etc. which are contained in the exhaust gas. The manner of operation of this sensor is basically like those mentioned at the 3rd Aspect.

By the provision of the 5th Aspect, the presence of the 2nd protective layer can prevent the oxygen storage component in the 1st protective layer from being poisoned by Si or the like in the exhaust gas, and ensures, even after long term use, to suppress the $\lambda$-point deviation (rich excursion) upon the rapid air increase as much as possible by the active presence of oxygen storage component in the 1st protective layer. This ensures the exact air-fuel ratio control at acceleration and steady running at the initial stage or after long use.

6th Aspect

Finally, according to the 6th Aspect of the present invention, there is provided a method of producing an oxygen sensor for air-fuel ratio control, by forming a protective layer on a side of the sensor element assigned to be exposed to an exhaust gas which comprises the steps of:

forming a first protective layer by immersing in a metal salt solution an oxygen storage component after formation of a heat-resistant metal oxide layer, and providing a second protective layer by formation of a heat-resistant metal oxide layer.

According to this method of the 6th Aspect, the oxygen sensor, particularly of the 5th Aspect, can be produced with high mass productibility, the sensor being such that can be used in a stable state for a long period of time without poisoned by Si etc. in the exhaust gas.

BRIEF DESCRIPTION OF THE DRAWINGS

FIG. 11 is a schematic view of an embodiment according to the 3rd Aspect, in which

FIG. 23(a) and (b) is graphs representing the results of TEST C(1), C(2) (particularly C(1)) in terms of the sensor output as a function ot time.

In the Figures, the reference symbols represent:

Figure 1:
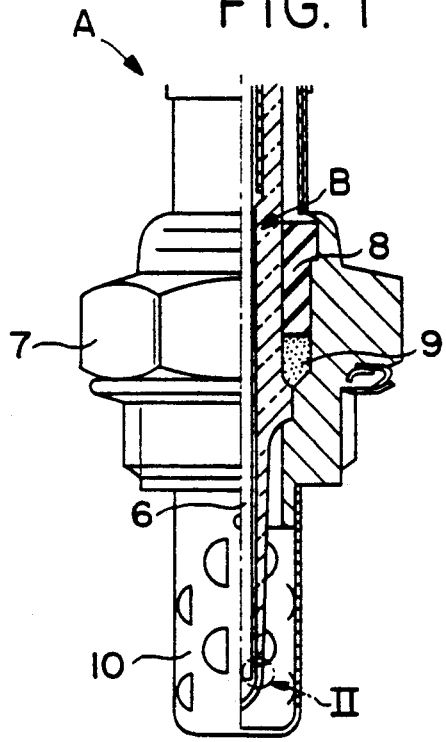
FIG. 1 is a semi-cross-sectional view showing a U-like-tube-type oxygen sensor according to the major Aspects of the present invention (particularly 1st Aspect)

| | |
|---|---|
| A | oxygen sensor, |
| B | oxygen sensor element, |
| 1 | the main body of the sensor element, |
| 1a | base portion, |
| 1b | spherically-protruded portion, |
| 3 | measuring electrode, |
| 4 | protective layer, |
| 4a, 5a | oxygen storage component (OSC), |
| 4b | noble metal catalyst, |
| 5 | 2nd protective layer, |
| 6 | heater, |
| 7 | housing, |
| 8 | caulking ring, |
| 9 | filler, and |
| 10 | protective tube. |

DETAILED DESCRIPTION OF THE INVENTION

In the following the preferred embodiments will be described for each Aspect.

1st Aspect

In the oxygen sensor of the 1st Aspect, the protective layer protects the electrodes, and more particularly, the measuring electrode from exhaust gases at an initial stage and after long term use. The protective layer may be made of heat-resistant metal oxide, for example, alumina, spinel, magnesia, beryllia, zirconia or the like, or a mixture of these materials. Particularly preferred is the protective layer mainly made of spinel, such as $MgO.Al_2O_3$ and the like. The OSC can thereby be carried in a highly dispersed state to provide its oxygen occlusive function for a long period of use, and a layer using spinel also has an excellent heat-resistive property. The protective layer may also be made of a stoichiometric compound and a nonstoichiometric compound. The layer may have a porosity of 5-20%, and more preferably, 7-20%, and the layer's thickness may be 30-200 $\mu$m, more preferably, 50-170 $\mu$m. The (measuring) electrode can be thereby securely protected without hindering its permeability to exhaust gases.

As the OSC included within the protective layer, non-stoichiometric compounds, for example, oxides of rare-earth elements or the like are used. Particularly preferred are cerium oxide and vanadium oxide, since these oxides have a strong function of occluding and releasing oxygen. In order to provide other materials with a function equal to that of these oxides, it is necessary to increase the amount or thickness. Hence, it would tend to cause clogging.

The OSC is present in 0.2-30 wt % (converted into the OSC's metal element) with respect to the heat-resistant metal oxide constituting the protective layer. If the content is less than 0.2 wt %, it is impossible to occlude a large amount of excess oxygen particularly at the moment of transient response. On the other hand, if the content exceeds 30 wt %, the function of occluding and releasing oxygen becomes too strong even at the steady running state, and the response frequency characteristic becomes too dull. However, when the protective layer is dipped in a metal-salt solution of the OSC after forming the protective layer in order to increase durability of the layer including the OSC as the protective layer, as will be described later, the content may be 0.2–8 wt %, and more preferably, 0.8–3 wt % in order to prevent clogging in the protective layer. If the content is less than the lower limit, the effect of the OSC becomes somewhat inferior. The content of the OSC is obtained by the following formula from a difference [X] in weight between before and after providing the protective layer (only of heat resistant metal oxide, without OSC incorporation) and an increment [Y] in weight after including the OSC:

$$\{Y \times (A/M)/X \times \text{ratio in area}\} \times 100$$

(where A: the atomic weight of the metal element of the OSC, M: the molecular weight of the OSC, ratio in area: the area of a portion which is immersed in an metal-salt solution of the OSC or on which a slurry of the OSC is coated/the entire surface area of the protective layer).

The OSC may be included on a portion preferably at least ½ of the entire surface area. If the portion is less than ½, the amount of exhaust gases which pass through a portion other than the portion where the OSC exists and reaches the (measuring) electrode becomes great, and variations in out put at that portion become dominant. The portion including the OSC is, more preferably, not less than 7/10 of the entire surface area.

The main body of the sensor element comprises a base portion and a plurality of spherical protrusions (termed spherically-protruded portion), and the protective layer is intermeshingly connected to the base portion via the spherically-protruded portion. Heretofore, the interface between the main body of the sensor element and the protective layer is provided as a flat interface, thus the protective layer has been such that is bonded to the main body only by a thermal fusion force produced upon forming the protective layer. At such an interface, however, there exists an electrode, and a noble metal, for example Pt, as a material for the electrode, which differs from the material for the main body of the sensor element and the heat-resistant metal oxide constituting the protective layer in various properties, such as coefficient of thermal expansion and the like. Accordingly, there occasionally occurs deterioration in durability, such as cracks, peeling-off and the like, during use at a portion where the (measuring) electrode exists and which is most important for the detection characteristics, of the sensor within the interface portion between the main body of the sensor element and the protective layer. However, by providing the spherically-protruded portion made of the same material as the main body of the sensor element corresponding to the interface between the main body of the sensor element and the protective layer, and particularly, to the position where the (measuring) electrode exists as in the present Aspect, the protective layer can be physically connected firmly to the main body of the sensor element utilizing the spherically-protruded portion, as it were, as a wedge. Hence, it is possible to stably protect the (measuring) electrode by the protective layer for a long period of time even under the condition of severe heat cycles, and to provide the above-described function of the OSC included within the protective layer. Moreover, by making the (measuring) electrode surface protrude and recede, i.e., irregular, due to the presence of the spherically-protruded portion, it is also possible to increase the surface area of the electrode to maintain a high λ-detection property with a narrow region.

The spherically-protruded portion may be made of the material for the main body of the sensor element, that is, a solid electrolyte ($ZrO_2$ or the like), or a semiconductive material ($TiO_2$, $CoO$ or the like). Concretely, where the material for the main body of the sensor element is made of an oxygen-ion-conductive solid electrolyte, the base portion of the sensor element may be made of, for example, $ZrO_2$-$Y_2O_3$ system, and the spherically-protruded portion may be made of $ZrO_2$-$Y_2O_3$ system or $ZrO_2$-$(CaO, MgO)$ system. Furthermore, the amounts of the stabilizer for zirconia may differ from each other under the same compositional system. The spherically-protruded portion may be provided on either of the inner side (the side closer to the sensor element) and the outer side (the side closer to the protective layer).

The spherically-protruded portion may be formed of an agglomeration of granulated particles, and may be present in a monolayer or multilayers. The particle size of the granulated particles may be 40–100 μm, and more preferably, 50–80 μm. If the particle size is less than 40 μm, the function as the wedge cannot be sufficiently provided. If the particle size exceeds 100 μm, there is a possible weakening in the adhesion force of the spherically-protruded portion with the main body of the sensor element (base portion) or the protective layer. The spherically-protruded portion may be distributed so that there exists a recess between adjacent spherically-protruded portion. The existence of the recesses can increase the bonding strength with the protective layer, and enlarge the surface area of the electrode.

2nd Aspect

In the following the 2nd Aspect of the present invention will be described relating to the method for producing the oxygen sensor, particularly ones mentioned on the 1st Aspect.

As for the formation of the spherically-protruded portion, the aforementioned spherical particles may be applied on the surface of the base material of the main body of the sensor element, and then fired to provide spherical particles having an average particle size of 40–100 μm and bonded solid with the main body. It is thereby possible to sufficiently leave protrusions and recesses as wedges even after the processing of depositing the electrode in the subsequent step, and to provide a strong bonding with the protective layer. That is, if the average particle size of the spherical particles after the firing is less than 40 μm, the wedge function cannot be sufficiently provided, and if the average particle size exceeds 100 μm, adhesion with the base material becomes weak. The particle size is more preferably 50–80 μm. Finer particles having an average particle size of not more than 10 μm may also be mixed to further increase strength. The base material for the main body of the sensor element and the spherical particles is preferably be cofired. The adhesion strength between the two materials can thereby be increased. The firing temperature may be 1400°–1500° C. Furthermore, the formation of the spherical particles may be performed after performing the processing of depositing the electrode. This process is particularly effective when the (measuring) electrode cannot be successfully formed in the case where the spherical particles have previously been applied and formed. That is, this process is effective when the electrode is formed by screen printing or the like on a green sheet, granulated particles are then applied thereon followed by cofiring.

The formation of the electrode is not limited to a particular method, but may be performed by a normal vapor-phase deposition, such as sputtering, vacuum deposition, or screen printing, as well as by a conventional plating process such as electroplating, chemical plating or the like.

The protective layer may be formed after the base material for the main body of the sensor element and the spherical particles have been fired to form the base portion of the main body of the sensor element and the spherically-protruded portion (the material for the protective layer may also be cofired as will be described later). As for the method of forming the protective layer, although there exist various methods, for example, methods in which a solution or powder of the material for the protective layer is applied by coating by a brush, immersing, spraying or the like followed by firing and the like, flame spraying, and more particularly plasma spraying, is preferred. The adhesion strength between flame-sprayed powders is great, so it is possible to provide arbitrary porosity and pore size by properly changing the conditions of the spraying. Furthermore, the electrode may be printed on a green sheet made of the material for the main body of the sensor element (for example, $ZrO_2$ solid electrolyte, $TiO_2$ or $CoO$ semiconductor, or the like) using a noble-metal paste, $Al_2O_3$ or the like as the material for the protective layer may subsequently be printed, and the resultant printed mass may be cofired. As the material for the protective layer, a compound which can form a metal oxide by pyrolysis, for example a hydroxide, a salt or the like, may be used other than the metal oxide. The particle size of the powder may be not more than 2 μm.

The OSC may be carried on the protective layer by immersing at least the protective layer in a metal-salt solution of the OSC followed by drying and firing. After the protective layer has been firmly applied and formed on the main body of the sensor element, the metal-salt solution of the OSC is impregnated within the (porous) protective layer. Hence, it is possible to carry the OSC in a state of high dispersion, and to prevent dissipation during the use. Accordingly, the above-described function of the OSC can be maintained stably for a long period of time.

As the metal salt of the OSC, a nitrate or an acetate may be used. In case of using a Ce salt, cerium nitrate may, for example, be used. The pH may be not more than 5. The metal-salt solution can thereby deeply penetrate within the protective layer to increase the adhesion strength of the OSC, and dispersion property is very high. More preferably, the pH is not more than 3. Since the metal-salt solution can thereby easily penetrate within the protective layer, it is possible to securely disperse Ce in flowing channels (pores) for exhaust gases within the protective layer. The immersing may be performed under vacuum or a reduced pressure of not more than 40 kPa (300 mmHg), and more particularly, not more than 26.6 kPa (200 mmHg), or a pressurized condition. The solubility of the metal salt can thereby be increased, and it is possible to perform high dispersion of the metal salt deeply and efficiently within the protective layer. If the pressure exceeds 40 kPa (300 mmHg), much time is required for the immersing processing or recovery, much metal salt adheres on the surface portion rather than within the protective layer, and there is a possibility of clogging in the protective layer. The immersing may be performed at a temperature no lower than room temperature, and more preferably, no lower than 20° C.

In performing the immersion processing, the protective layer has previously been formed by flame spraying or the like, and is in a state firmly connected to the main body of the sensor element by the spherically-protruded portion. Accordingly, the bonding property between the main body of the sensor element and the protective layer is not hindered even if the metal-salt solution of the OSC is impregnated within the protective layer by the immersion processing. Moreover, since the protective layer is formed porous (has continuous open pores) and the immersion processing is performed thereafter, the metal salt can be carried in a part of the continuous open pores in the porous protective layer in a state of high dispersion. Hence, the main body of the sensor element and the electrode are securely protected by the protective layer under the condition of severe heat cycles, and the function of the OSC can be very efficiently provided even after durability tests.

The immersion of the protective layer is performed by holding the sensor element portion of the sensor downward. In this case, the portion up to 95% from the distal (lower) end of the protective layer may be immersed. If the immersed portion exceeds 95%, the metal-salt solution of the OSC adheres on a collar portion (flanged portion) of the sensor element which is assigned to be a conductive portion, and there is a possibility of hindering the conductive property of that portion upon use. A heat-resistant metal oxide, for example, alumina or spinel, may be included within the metal-salt solution, and the protective layer may be immersed in the resultant solution. In this case, however, there is a possibility of decreasing durability.

The amount of the OSC carried by the impregnation may be 0.2–8 wt % (converted into the metal element of the OSC) with respect to the heat-resistant metal oxide. More preferably, the amount may be 0.8–3 wt %. The upper limit is for preventing clogging of the protective layer and cracks in the protective layer when the sensor is used. The amount less than the lower limit causes somewhat inferior effect of the OSC.

After the impregnation of the metal-salt solution of the OSC by the immersion processing, the protective layer may be subjected to heat treatment in an oxidizing atmosphere at a temperature of 300°–850° C. The metal salt of the OSC is thereby subjected to pyrolysis, water content is volatilized, and the metal salt can thus be converted into the OSC. If the temperature is less than 300° C., such function is insufficient. On the other hand, if the temperature exceeds 850° C., $O_2$ is occasionally adsorbed on the electrode and the like. In addition, occlusion of oxygen on the OSC temporarily increases, and there is a possibility of difficulty in release of the occluded oxygen during use. The temperature is, more preferably, not more than 800° C. If the heat treatment is performed under a reducing atmosphere, there is produced, for example, toxic NO in the case of a nitrate. Hence, handling becomes troublesome.

3rd Aspect

In the following, preferred embodiments of the oxygen sensor of the 3rd Aspect of the present invention will be described.

In the oxygen sensor of the 3rd Aspect, the 1st protective layer is disposed closest to the (measuring) electrode, and directly protects the (measuring) electrode from the exhaust gas. The 1st protective layer may be constructed in a similar fashion as the protective layer of the 1st Aspect.

The noble metal catalyst contained in the 1st protective layer is preferably comprised mainly of Pt, e.g., containing 80 wt % or more of Pt, which may serve to promote the oxidizing reaction with CO and/or HC among the unburnt components in the exhaust gas. With the noble metal being comprised mainly of Rh and Pd, the reducing reaction of $NO_x$ among the unburnt components can be promoted. The amount of the incorporated noble metal should be 0.01–5 wt % relative to the heat-resistant metal oxide. Below this lower limit there is little effect thereof, while above the upper limit it tends to clogging. Under the exhaust gas with a high concentration (i.e., rich gas), about 1 wt % is preferred. Above 3 wt %, there might be fear of crack formation through adsorbance or reaction of the unburnt components contained in a great amount in the gas, by or with the noble metal catalyst. This catalyst may be dispersed either uniformly or nonuniformaly in the entire region of the 1st protective layer. For instance the noble metal can be dispersed with a higher concentration at the distal end which is exposed to a higher amount of unburnt components. The kind of catalyst may be changed from region to region in the 1st protective layer.

As for the 2nd protective layer, it can be formed of the heat-resistant metal oxide that is the same as those of the 1st protective layer, e.g., spinel, alumina, and the like stoichiometric compounds, or nonstoichiometric compounds such a $TiO_{2-x}$ (x=0.02–0.3), NiO and/or the like. The 2nd protective layer made of these materials can carry the OSC in a highly dispersed state to effectively develop the oxygen occluding/releasing function, with high heat resistance. A mixture of the stoichiometric and nonstoichiometric compounds may be used, too, as the 2nd protective layer. The porosity (open pore rate) of the 2nd protective layer is greater than (preferably, about 1.5 times) that of the 1st protective layer, e.g., with a porosity of 8–35%. By this measure, the deterioration in the permeability of exhaust gas and the sensor responsibility can be suppressed while effectively exhibiting the oxygen occluding function. From the same point of view, the 2nd protective layer is constructed thinner than the 1st protective layer, e.g., at a thickness of preferably 10–50 μm, more preferably 20–35 μm.

The OSC incorporated in the 2nd protective layer may be such that employed in the protective layer of the 1st Aspect. Preferably, the OSC is distributed over at least a half of the entire surface area of the 2nd protective layer. If it is less than the half, the amount of exhaust gas which reaches the measuring electrode passing through an area without OSC increases so that the output from this area becomes dominant. 7/10 or more of the entire area is more preferred to include the OSC.

4th Aspect

In the following preferred embodiments of the 4th Aspect of the present will be set forth.

In the method for producing the A/F (air-fuel) ratio control oxygen sensor, according to the third Aspect of the present invention, the first protective layer may be formed in the same way as in the second Aspect.

The catalyst may be supported by the first protective layer by immersing (or dipping) in a noble metal salt solution followed by drying and heat treating. The concentration of the solution should be maintained in a range in which the catalyst is dispersed sufficiently and no clogging is brought about during impregnation. If the catalyst is Pt, a $H_2PtCl_6$ solution may be used as the solution containing Pt in a sufficiently dispersed state. The Pt concentration in the solution may be set to 0.01 to 5 g/l. With the Pt concentration less than 0.01 g/l, the catalytic action becomes insufficient, whereas, with the Pt concentration in excess of 5 g/l, the first protective layer tends to be clogged and the sensor response properties are lowered. The immersing operation may be performed under a reduced or pressurizae pressure as desired. The noble metal containing salt solution penetrates deep in the pores of the first protective layer so that the noble metal catalyst may be dispersed uniformly in the first protective layer. The heat treating temperature may be 400° to 700° C.

The first protective layer may also be formed by coating a slurry of a heat resistant metal oxide and noble metal on the main body of the sensor element. However, in such case, the noble metal catalyst becomes poor in durability and the expensive noble metal may be used in vain because the catalytic function of noble metal cannot be displayed effectively.

The second protective layer is preferably formed in the same manner as is the first protective layer. In forming the second protective layer, spinel ($MgO-Al_2O_3$) may be applied by plasma-spraying, or fine powders of $Al_2O_3$ and/or $TiO_2$ may be applied by a brush and fired (or baked) subsequently. These fine powders are preferably of a particle size of not more than 1 μm. In this manner, the second protective layer may be of a fine open pore structure so that the oxygen occluding and releasing function proper to the OSC supported by the second protective layer may be exhibited more effectively. On the other hand, when the exhaust gas intrudes into the sensor during use, Si or C as poisoning ingredients may be securely captured by this second protective layer. The element may be then immersed in an OSC metal salt solution, dried and heat treated. By strongly bonding the second protective layer on the first protective layer and impregnating the porous second protective layer with the OSC metal salt solution, the OSC may be supported in a highly dispersed state and prevented from flying off during use. Thus the above mentioned function of the OSC may be maintained stably for a prolonged period of time.

The type of the OSC metal salts, immersing conditions and the incorporated amounts may be selected in the same manner as in the second Aspect described hereinbefore.

Meanwhile, when the second protective layer is previously formed by flame spraying, the OSC metal salt solution is hardly impregnated in the first protective layer. The protective layer is immersed with its detecting portion of the sensor directed downwards. In such case, a portion of the protective layer which accounts for not exceeding 95% counted from the lower end (distal end) is preferably dipped in the OSC metal salt solution, as mentioned previously. The second protective layer may also be dipped in a metal salt solution containing heat-resistant metal oxides, such as alumina or spinel. However, in such case, the bonding strength to the second protective layer and to the measuring electrode may be too weak resulting in a shorter durability of the sensor.

In forming the second protective layer, the first protective layer may be coated by means of a slurry composed of the material of the main body of the (second) protective layer and OSC, and the resulting mass may be fired subsequently. If the formation of the main body of the protective layer and the supporting of the OSC are performed simultaneously, the OSC may be bonded more strongly to prevent the flying off during the use to exhibit the oxygen occluding and releasing function more stably for a prolonged period of time. By using a slurry, the binder or the like may dissipate (or be volatalized) during formation to realize a desired porosity and pore diameter more easily. The slurry may be obtained by mixing a binder and a solvent as conventionally. Coating may be by brush coating, immersion or spraying, as desired. For mixing the material of the protective layer and OSC, the powders of the material of the protective layer may be impregnated with the OSC metal salt solution. Homogeneous mixing may thereby be achieved. The materials of the protective layer may include, besides metal oxides, those compounds which upon thermal decomposition may form metal oxides, such as hydroxides or salts. The particle size of the powders is preferably 2 $\mu$m or less and more preferably 0.3 to 1.5 $\mu$m because sinterability and bonding strength and improved so that the second protective layer is less likely to peel off during use of the sensor. Heat treatment (sintering or calcination of the porous protective layer) is preferably performed at a temperature of 600° to 900° C. under an oxidizing atmosphere.

5th Aspect

In the following preferred embodiments of the 5th Aspect will be set forth.

With the oxygen sensor of the 5th Aspect of the present invention, the first protective layer is disposed in proximity to the electrode and carries the OSC to protect the measuring electrode from direct contact with the exhaust gas and a prevent deviation of the $\lambda$-point due to sudden increase in the air amount. The first protective layer may be similar in structure to the protective layer of the 1st Aspect and of a thickness in the range from 30 to 200 $\mu$m and preferably from 50 to 170 $\mu$m. The measuring electrode may be protected reliably without causing hindrance to the permeability of the exhaust gas.

The OSC contained in the first protective layer may be similar to that contained in the protective layer of the 1st Aspect.

Preferably, the OSC is contained in one half or more of the total upper surface area of the first protective layer. If OSC is contained in less than one half the surface area of the first protective layer, more amount of exhaust gas may reach the electrode passing through the area devoid of OSC, so that output fluctuations in this area become dominant. Preferably, the OSC is contained in a surface area which is 7/10 or more of the total surface area of the first protective layer.

The second protective layer may be similar in construction to the second protective layer of the 3rd Aspect. This second protective layer has a greater porosity (open pore), (preferably, about 1.5 times) than the first protective layer, e.g., to be 30–50% for suppressing diterioration in gas flowability an responsibility of the sensor while maintaining oxygen occluding function. In one same point of view the second protective layer is thinner than the first protective layer, e.g., to be 10–50 $\mu$m, preferably 30–35 $\mu$m.

6th Aspect

In the method for producing the air-fuel ratio control oxygen sensor, according to the 6th Aspect of the present invention, the first protective layer may be formed in the same way as the protective layer of the 1st Aspect. The OSC may be carried by the first protective layer in the same way as in the 3rd and 4th Aspects. The types of the OSC metal salts, immersing conditions and the supported amount may be selected in the same way as in the 1st and 2nd Aspects.

As described previously, the noble metal may be supported by the second protective layer (provided that such noble metal should not co-exist with the OSC). Since noble metal serves to bring the unburnt components in the exhaust gas to the equilibrium the deviation toward the lean side of the $\lambda$-point caused by the unburnt components may be minimized. If the noble metal is comprised mainly of Pt, for example, not less than 80 wt % Pt of the entire catalyst, oxidizing reaction of CO and HC among the unburnt components may be promoted, whereas, if it is comprised mainly of Rh and Pd, reducing reaction of $NO_x$ among the unburnt components can be promoted. The supported amount of the catalyst may be in the range of 0.01 to 5 wt % relative to the weight of the heat-resistant metal oxides constituting the second protective layer. The supported amount less than 0.1 wt % is of little effect, whereas the supported amount in excess of 5 wt % may tend to cause clogging under conditions in which the catalyst is exposed to rich exhaust gases (with high concentrations of unburnt components). The supported amount is preferably about 1 wt %. If the amount exceeds 3 wt %, unburnt components that exist in a larger amount may be adsorbed to or react with the noble metal layer to cause cracks in the protective layer. It is not preferred that noble metal be supported by the first protective layer simultaneously with OSC, since the oxygen occluding and releasing function proper to OSC may be intensified excessively under the strong influence of the noble metal to lower the control frequency of the sensor, causing deviation from the range or window of the ternary catalyst of the exhaust gas purification system.

For carrying the noble metal on the second protective layer (however, without the OSC), the first protective layer may be coated by a slurry composed of the material of the main body of the protective layer and noble metal to form the second layer, and the resulting mass may be fired subsequently. If the formation of the main body of the protective layer and the supporting of the catalyst are performed simultaneously, the catalyst may be bonded more strongly to prevent the flying off during use of the sensor to exhibit the oxygen occluding and releasing function stably for a prolonged period of time. By using a slurry, the binder or the like may dissipate during the layer formation to realize the desired pore ratio and pore diameter more easily. The slurry may be obtained by mixing the binder and the solvent as conventionally. Coating may be by brush coating, immersion or spraying, as desired. For mixing the material of the protective layer and the supporting catalyst, the powder of the material of the protective layer may be impregnated with the noble metal salt solution. Homogeneous mixing may thereby be achieved. The materials of the second protective layer may include, besides metal oxides, those compounds which upon thermal decomposition may form metal oxides, such as hydroxides or salts. The particle size of the powders is preferably 2 μm or less and more preferably 0.3 to 1.5 μm because sinterability (at the heat treatment) and bonding strength are improved so that the second protective layer becomes less likely to peel off during use of the sensor. Heat treatment is preferably performed at a temperature of 600° to 900° C. under an oxidizing atmosphere.

When supporting the noble metal on the second protective layer, the second protective layer may be formed on the first protective layer and at least the main body of the second protective layer may then be dipped in the noble metal salt solution, dried and heat treated at 400° to 700° C. The concentration of the solution is determined in such a manner that the catalyst may be dispersed sufficiently therein and no clogging is produced by impregnation. For example, the amount of the catalyst may be determined in the same way as for the first protective layer in the 3rd and 4th Aspects.

The following further arrangements, for example, may be employed for the oxygen sensor of the present invention:

(a) A heater may provided in the vicinity of the sensor element in which case the oxygen occluding and releasing action proper to the OSC and the catalytic action proper to the noble metal may be displayed stably, respectively.

(b) A third protective layer may be provided for covering the second protective layer to improve durability and display the above functions of the noble metal and OSC more stably for a further extended period of time.

(c) A plurality of spherical protrusions (spherical protruding portion) may be interposed (i) between the sensor element and the first protective layer (also in the 3rd through 6th Aspects, as the case with the 1st and 2nd Aspects), or (ii) between the first and the second protective layers to prevent peeling and improve durability of the protective layer.

(d) The components of the group IIa elements (under the International version of the Periodic Table) especially non-oxides of Ca or Mg, such as $CaCO_3$, $CaCl_2$ or $Mg(NO_3)_2$ may be contained in the protective layers, above all in the outer layer, to prevent possible poisoning by Si even when Si components are contaminants of the exhaust gas.

The present invention may be applied extensively as various types of sensors for, e.g., air-to-fuel ratio control, that is, theoretical air-to-fuel ratio control, dilute (lean state) air-to-fuel ratio control, full range air-to-fuel ratio control, as well as for sensors provided with pumping cell elements, solid electrolyte ($ZrO_2$) type sensors, or semiconductor ($TiO_2$, $CoO$) type sensors, or else.

EXAMPLES

Example A

Figure 2:
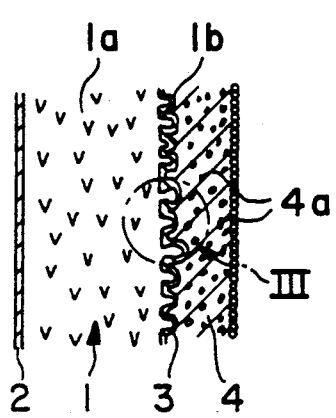
FIG. 2 is a schematic view of an enlarged cross section of portion II in FIG. 1.
Figure 3:
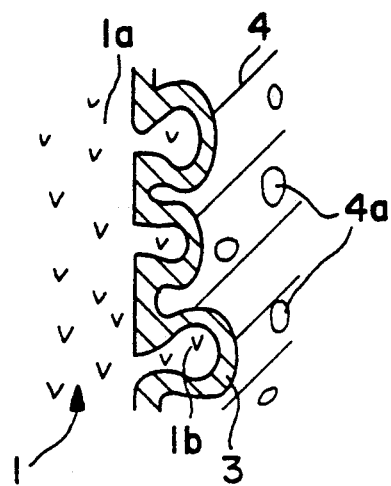
FIG. 3 is a schematic view of an enlarged cross section of portion III in FIG. 2.

U-tube-like oxygen sensors (Sample Nos. A1-A4, Comparative Sample Nos. AI-IV) as shown in FIGS. 1-3 were obtained by the following step. The concrete composition for each sample is shown in Table 1.

Step 1:
5 mole % $Y_2O_3$ having a purity of 99.9% was added to $ZrO_2$ having a purity of not less than 99% and mixed, and the resultant mixture was calcined at 1300° C. for 2 hours.

Step 2:
With adding water, the calcined material was pulverized in a ball mill in a wet state until 80% of the particles had particle sizes of not more than 2.5 μm.

Step 3:
A water-soluble binder was added, and spherical granulated particles having an average particle size of 70 μm were obtained by spray drying.

Step 4:
The powder obtained in step 3 was formed into a desired tube-like shape (the shape of a U-tube) by rubber pressing and dried. The formed material was then ground into a predetermined shape by a grinding tool.

Step 5:
A slurry, which was made by adding a water-soluble binder, cellulose, sodium glycolate and a solvent to the granulated particles obtained in step 3, was applied on the outer surface of the sample obtained in step 4.

Step 6:
After being dried, the sample obtained in step 5 was sintered at 1500° C. for 2 hours. The portion corresponding to the sensor element portion had a length in axial direction of 25 mm, an outer diameter of about 5 mmϕ, and an inner diameter of about 3 mmϕ.

Step 7:
A Pt measuring electrode layer 0.9 μm thick was deposited on the outer surface by electroless plating, and then baked at 1000° C.

Step 8:
$MgO.Al_2O_3$ (spinel) powder was plasma sprayed to form a protective layer about 150 μm thick.

Step 9:
A Pt reference electrode layer was formed on the inner surface in the same manner as step 7.

Step 10:
Cerium nitrate was dissolved in a solution made by diluting nitric acid with water to prepare nitric-acid solutions of cerium nitrate having various concentrations.

Step 11:
The protective layer of the sensor element obtained by steps 1–9 was dipped in the solution obtained by step 10, left for about 10 minutes under a pressure of 50–250 mmHg to impregnate cerium nitrate within the protective layer. The protective layer was then processed at 600° C. in air to carry cerium oxide in the protective layer.

Step 12:
After inserting a sensor element 1 into a housing 7, a ring 8 for calking and a filler 9, such as talc and the like, were charged therein to fix a sensor element B within the housing 7.

Step 13:
Leads were connected to electrodes 2 and 3 via terminals.

Step 14:
A protective tube 10 was disposed covering the distal-end portion of the sensor element B, and the distal end of the housing 7 and the rear end of the protective tube 10 were welded together.

Step 15:
An outer tube was covered to obtain the oxygen sensor.

Tests
For each of the samples thus obtained, the following tests were performed.

A(1) Each sample was subjected to a durability test with temperature cycles between a temperature not higher than 200° C. (20 minutes) and a temperature not lower than 900° C. (30 minutes) for 500 hours placed on a real vehicle. Subsequently, the sample was dropped onto a concrete floor from a height of 50 cm 5 times, and the appearance was then evaluated. The results of the evaluation are represented by the following marks.

No peeling etc.: A
Partly peeled: B
Entirely peeled: x

Figure 8A:
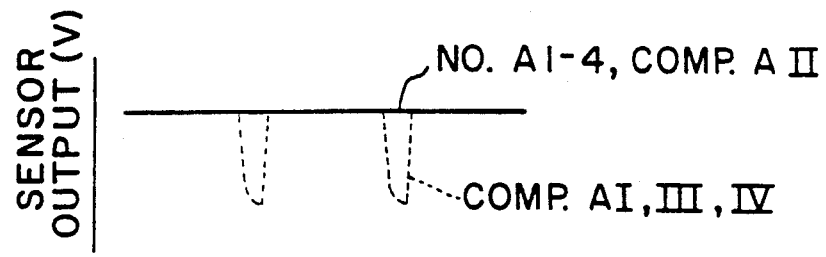
FIG. 8 (a) and (b) is a graph showing the result of test A(2), and shows a relationship between time and sensor output.
Figure 8B:
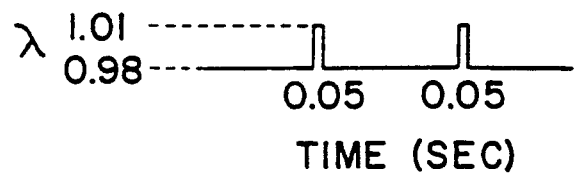

A(2) Each sample after the above-described test A(1) was mounted on a propane burner apparatus, the burner was burnt, the atmosphere was temporarily switched from $\lambda \approx 0.98$ to 1.1 to shift to the lean side as shown in FIG. 8, and the output state of the sensor at that time was investigated. The results of the evaluation are represented by the following marks.

Almost no change in the output: A
Changed about 100 mV: B
Changed not less than 200 mV: x The results are shown in the following table 1 and FIG. 8.

As is evident from FIG. 8, in test A(2), in Comparative Sample No. AI (described above), Comparative Sample No. AIV (described above) and Comparative Sample No. AIII (an oxygen sensor having only a spinel protective layer), when the A/F ratio temporarily moves from the nearly theoretical value (excess air ratio $\lambda = 0.98$) to the lean side ($\lambda = 1.1$), even if the A/F ratio returns to the nearly theoretical value ($\lambda = 0.98$), a decrease largely deviating from the rich side with respect to the A/F curve (rich excursion) is produced due to a delay in response. On the other hand, in Example Nos. A2–A4, by first storing oxygen at the moment of increasing the amount of air due to the presence of the OSC, the timing of outputting a lean signal is delayed, and, as a result, the period during which the lean signal is being outputted is shortened. Accordingly, the above-described rich excursion never occurs, and A/F ratio rapidly returns near the theoretical value after the termination of increasing the amount of air. In Example Sample No. A1 and Comparative Sample No. AII as

TABLE 1

| Sample No. A | Spherically-protruded portion | Protective layer Metal oxide | OSC | Amount[1] (wt %) | Degree of vacuum (mmHg) | Test A (1) | (2) |
|---|---|---|---|---|---|---|---|
| 1 | yes | Spinel[2] | $CeO_2$ | 1 | 50 | A | B |
| 2 | ↑ | ↑ | ↑ | 5 | 50 | A | A |
| 3 | ↑ | ↑ | ↑ | 5 | 150 | A | A |
| 4 | ↑ | ↑ | ↑ | 5 | 250 | A | A |
| *I[3] | ↑ | ↑ | ↑ | 2 | 100 | B | X |
| *II | — | ↑ | ↑ | 5 | 50 | B | B |
| *III | yes | ↑ | — | — | — | A | X |
| *IV | ↑ | ↑ | $Al_2O_3 + CeO_2$ | 10 | — | X | X |

1 mmHg = 133.3 Pa

[1]This amount is for OSC/metal oxide, and is a value converted into the metal element (Ce) of OSC.
[2]Spinel: $MgO \cdot Al_2O_3$
[3]*: Comparative sample As will be apparent from FIG. 8, in Test A(1), in Comparative Sample No. AIV (an oxygen sensor produced nearly in the same manner as in the example disclosed in JP Patent Kokai Publication No. 61-79155 (1986), in which $CeO_2$ was formed not by dipping in a Ce-salt solution, but by coating a slurry of mixed powders of $\gamma$-$Al_2O_3$ and and $CeO_2$, and which is 20–30 $\mu$m thick), a layer made of $Al_2O_3$ and $CeO_2$ formed on a spinel protective layer peeled from the spinel protective layer. Accordingly, this sample is remarkably inferior in durability under heat cycles. In Comparative Sample No. AII (which has a protective layer having the same composition formed by being dipped in a Ce-salt solution under the same condition of vacuum as in Example Sample No. A2, but does not have spherically-protruded portion), a part of the protective layer peeled. Furthermore, in Comparative Sample No. AI (in which $CeO_2$ was formed by not dipping in the Ce-salt solution, but by coating a slurry of only $CeO_2$ powder) as well, most of $CeO_2$ was present formed as a layer in the surface of a spinel layer, and a part of the $CeO_2$ peeled. On the other hand, in Example Sample Nos. A1–A4 and Comparative Sample No. AIII, no such peeling was observed, and the protective layer carrying $CeO_2$ was stably fixed on the main body of the sensor element to protect the main body of the sensor element and the electrode. Hence, it has become evident that these samples have very excellent durability under the conditions of severe heat cycles, and have excellent detection characteristic of $\lambda$ and response property even used for a long period of time under the conditions of severe heat cycles.

well, nearly the same effect was observed.

Accordingly, Example Sample Nos. A1–A4, and particularly Sample Nos. A2–A4 show excellent detection characteristics of $\lambda = 1$ and sufficient response properties. Hence, the samples are extremely useful particularly in an air-fuel ratio control system in which the gas flow rate of the exhaust system is large. In addition, even at the moment of a rapid increase in the amount of air when performing acceleration and the like, no deviation in $\lambda$-point is produced, and it is possible to perform an exact air-fuel ratio control. Thus, the purification characteristic for toxic materials can be maintained at a high level without deviating from the range of a ternary catalyst in an exhaust-gas purification system even if used for a long period of time under the conditions of severe heat cycles.

EXAMPLE B-1 (3rd and 4th Aspects)

Figure 9:
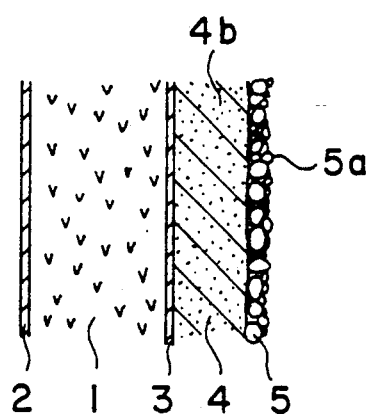
FIGS. 9 and 10 are schematic views of an enlarged cross section of portion II in FIG. 1, according to the 4th Aspect (step 11(a) and step 11(b), for 4(a) and 4(b) Aspects, respectively)
Figure 10:
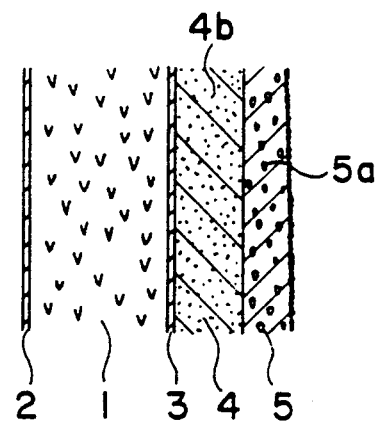

U-tube shaped oxygen sensors shown in FIGS. 1, 9 and 10 (Sample Nos. B1 to B13 and comparative Sample Nos. BI to BIII) were produced by the following step. The concrete composition of each sample is shown in Table 2.

Figure 6:
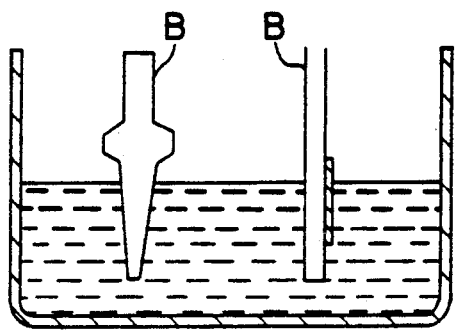
FIG. 6 is a cross-sectional view showing an immersing process of a metal-salt solution of an OSC (step 11 in Example A etc.)
Figure 7:
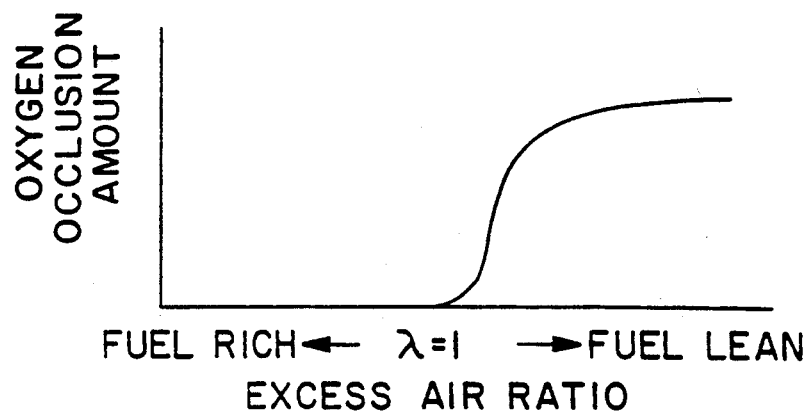
FIG. 7 is a graph showing a relationship between the amount of oxygen occlusion of the OSC and excess air ratio $\lambda$.

Steps 1 to 9:
Same as the steps 1 to 9 of Example A.
Step 10:
The first protective layer was dipped, as shown in FIG. 6, in a $H_2PtCl_6$ solution containing 0.05 g/l to 1 g/l of Pt and/or a $RhCl_3$-$xH_2O$ solution containing 0.05 g/l of Rh and allowed to stand for about five minutes under a pressure of 6.7 to 13.3 kPa (50 to 100 mmHg) to impregnate noble metal salts into the first protective layer. This operation of impregnation was repeated several times. Then the sample piece was heat treated in air at 600° C. so that the noble metal will be carried by the first protective layer.

Step 11:
Formation of a second protective layer (a) Cerium nitrate was mixed with water and with powders of $Al_2O_3$ having an average particle size of 0.5 μm or powders of $TiO_2$ having a mean particle size of 0.3 μm. The resulting mixture was coated on the first protective layer and heat treated in air at 600° C.

(b) For preparing the Sample Nos. B4, B5, B10 and B11, a spinel layer 20 μm thick was again formed by flame spraying. The resulting product was dipped in a cerium nitrate solution, as shown in FIG. 6, for impregnation. The resulting product was heat treated in air at 600° C. so that the cerium nitrate is carried by the second protective layer.

Steps 12 to 15:
Same as the steps 12 to 15 of Example A.

EXAMPLE B-2 (relating to 3rd and 4th Aspects, particularly)

Figure 4A:
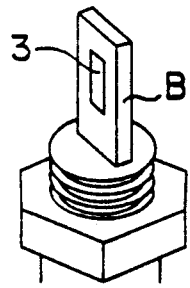
FIG. 4 is a perspective view showing another embodiment of the oxygen sensor according to the present invention, in which FIG. 4 (a) shows a plate-like oxygen sensor, and FIG. 4 (b) shows a cylindrical oxygen sensor.
Figure 13:
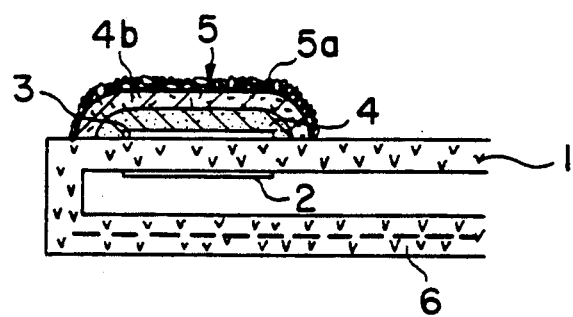
FIG. 13 is a cross sectional view showing an embodiment of a plate type oxygen sensor.

Plate-like (or sheet-like) oxygen sensors (Sample Nos. B14 and B15 and a comparative Sample BVI) as shown in FIGS. 4(a) and 13 were produced by the following steps.

Step 1:
A sheet comprised mainly of 5 mole % of ($ZrO_2$+$Y_2O_3$) was prepared by the doctor blade method in a thickness of 0.8 mm.

Step 2:
Electrodes formed of a paste comprised mainly of Pt and also containing an organic binder and a solvent were printed by the screen printing method on both sides of the sheet in a thickness of 20 μm.

Step 3: (first protective layer)
A paste comprised mainly of $Al_2O_3$ and also containing an organic binder and a solvent and a small quantity of starch to render the paste porous was coated to a thickness of 30 μm to cover the electrodes (formation of a porous $Al_2O_3$ layer as a first protective layer)

Step 4: (Steps 4 to 6: preparation of counterpart green sheet)
A paste comprised mainly of $Al_2O_3$ and also containing an organic binder and a solvent was coated on both sides of a sheet having the same composition and thickness as in Step 1. (Substrate sheet for heater)

Step 5:
A heater pattern of the paste of Step 2 was printed on the resultant substrate sheet of Step 4 to a thickness of 20 μm.

Step 6:
An $Al_2O_3$ layer was coated in the same way as at Step 4 but only covering the heat pattern surface. (upper layer of heater)

Figure 17:
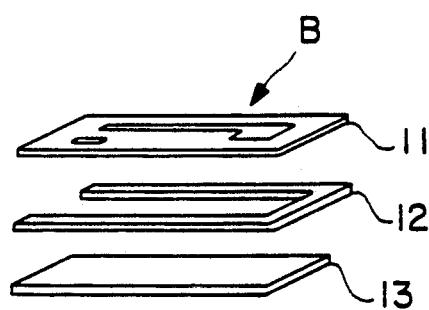
FIG. 17 is an exploded perspective view to elucidate step 7 at Example B-2.

Step 7:
A spacer sheet 12 was prepared by cutting a sheet having the same composition and thickness as in Step 1. As shown in FIG. 17, the spacer sheet 12 was interposed between the green sheet 11 obtained by the steps 1 to 3 with the electrode printed thereon and a counterpart green sheet 13 obtained by the steps 4 to 6 with the inner heater pattern (not shown in the Figure) and bonded together under application of heat and pressure.

Step 8:
After the binder (resin) was removed at 400° C. for 24 hours, the product from Step 7 was sintered at 1500° C. for four hours.

Step 9:
Noble metal salts were impregnated into the first protective layer by dipping in a noble metal salt solution similar to that used at step 10 of Example B-1. Heat treatment was then performed in air at 600° C. so that the noble metal catalyst is carried by the first protective layer.

Step 10:
Formation of second protective layer

Similarly to the Step 11(b) of Example B-1, a spinel layer was formed by flame spraying to a thickness of 20 μm.

Step 11:
After dipping in a cerium nitrate solution, heat treatment in air at 600° C. was performed.

Figure 18:
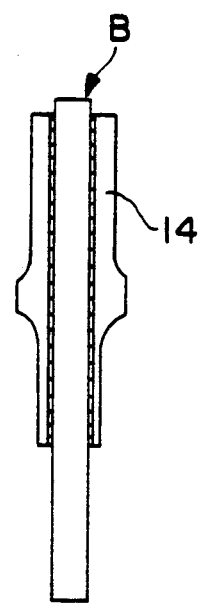
FIG. 18 is a cross sectional view illustrating step 12 of Example B-2.

Step 12:
On both sides of an element, thus prepared, a pair of supporting members 14 were bonded by glass sealing, as shown in FIG. 18.

Steps 13 to 16: (assembling to make up sensor)
Same as Step 12 to 15 of Example B-1.

TESTS
On the samples, obtained in the above described manner, the following tests were conducted.

TEST B(1)
The samples were attached to an engine of an actual vehicle and the sensor output was measured gradually changing the A/F ratio (i.e., excess air ratio λ).

Figure 14:
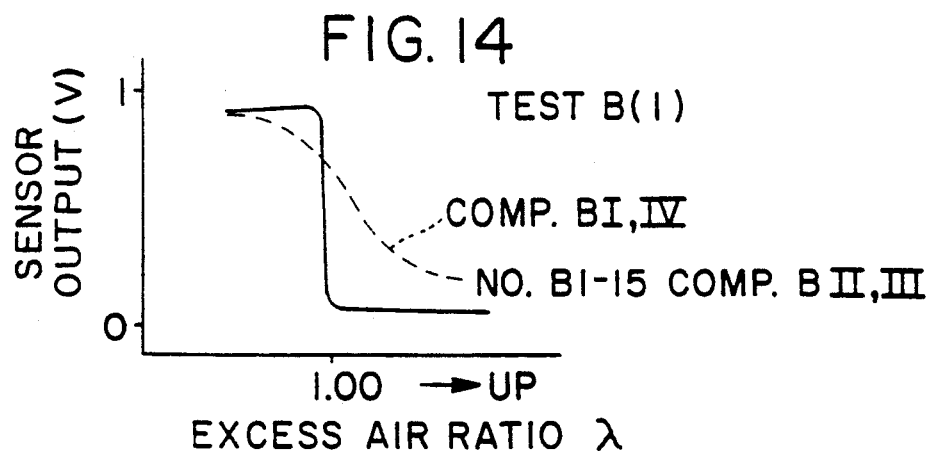
FIG. 14 is a graph showing the result of TEST B(1) to represent the relation of the sensor output versus the excess air ratio ($\lambda$)

The results are shown in FIG. 14.

Figure 15:
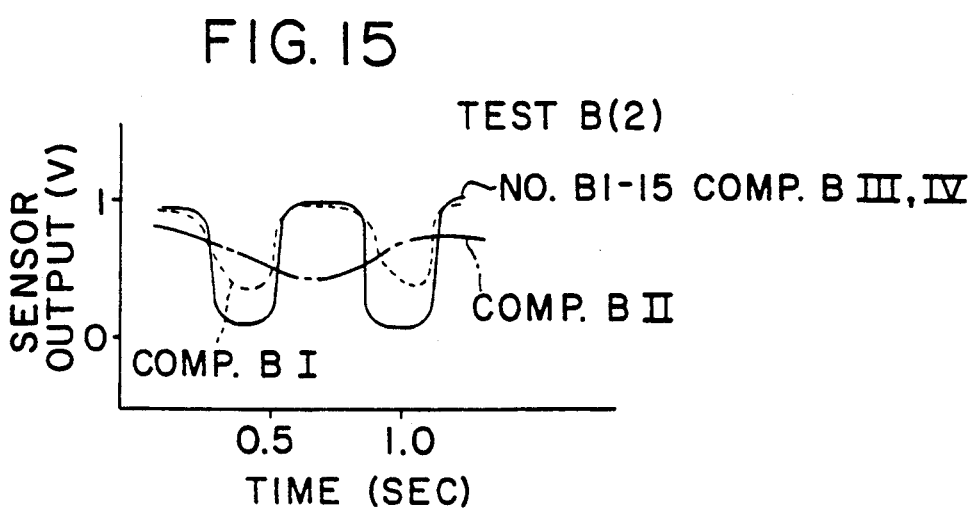
FIG. 15 is a graph showing the result of TEST B(2) to represent the sensor output as a function of time.

TEST B(2)
The samples were attached to an engine of an actual vehicle and, with the air-fuel ratio being changed between A/F 12 and A/F 16 at the period of 2 Hz, the sensor output waveform was investigated. The results are shown in FIG. 15.

Figure 16A:
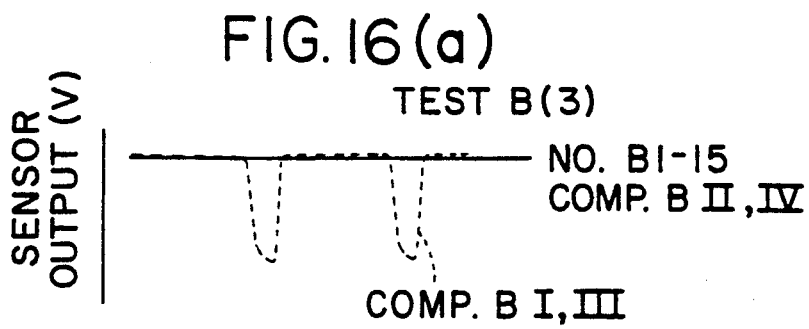
FIG. 16 (a) and (b) is a graph showing the result of TEST B(3) to represent the sensor output as a function of time.
Figure 16B:
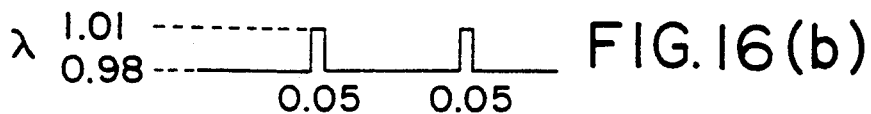

TEST B(3)
The samples were attached to a propane burner device and the burner was subjected to combustion. The atmosphere was transiently switched from excess air ratio λ≈0.98 to 1.1 towards the lean side, as shown in FIG. 16, and the prevailing sensor output was investigated. The results are shown in Table 2 and FIGS. 14 to 16.

TABLE 2

| Sample No. B | 1st protective layer | | | 2nd protective layer | | | Remarks[5] Step |
|---|---|---|---|---|---|---|---|
| | Metal oxide | Noble metal | Amount[1] (wt %) | Metal oxide | OSC | Amount[2] (wt %) | |
| 1 | Spinel[3] | Pt | 0.02 | $Al_2O_3$ | $CeO_2$ | 3 | 11 (a) |
| 2 | ↑ | ↑ | 0.02 | ↑ | ↑ | 20 | ↑ |
| 3 | ↑ | Pt + Rh | 0.02 | $TiO_2$ | ↑ | 10 | ↑ |
| 4 | ↑ | Pt | 0.02 | Spinel | ↑ | 1 | 11 (b) |
| 5 | ↑ | ↑ | 0.02 | ↑ | ↑ | 5 | ↑ |
| 6 | ↑ | ↑ | 0.02 | $Al_2O_3$ | ↑ | 30 | 11 (a) |
| 7 | ↑ | ↑ | 0.5 | ↑ | ↑ | 5 | ↑ |
| 8 | ↑ | ↑ | 0.5 | ↑ | ↑ | 10 | ↑ |
| 9 | ↑ | ↑ | 1 | ↑ | ↑ | 10 | ↑ |

TABLE 2-continued

| Sample No. B | 1st protective layer | | | 2nd protective layer | | | Remarks[5] Step |
|---|---|---|---|---|---|---|---|
| | Metal oxide | Noble metal | Amount[1] (wt %) | Metal oxide | OSC | Amount[2] (wt %) | |
| 10 | ↑ | ↑ | 1 | Spinel | ↑ | 10 | 11 (b) |
| 11 | ↑ | ↑ | 5 | ↑ | ↑ | 10 | ↑ |
| 12 | ↑ | ↑ | 5 | TiO$_2$ | ↑ | 10 | 11 (a) |
| 13 | ↑ | Pt + Rh | 0.5 | ↑ | ↑ | 20 | ↑ |
| *I | Spinel | — | — | — | — | — | — |
| *II[4] | ↑ | — | — | — | CeO$_2$ (+ Pt) | — | — |
| *III | ↑ | Pt | — | — | — | — | — |
| 14 | Al$_2$O$_3$ | Pt | 0.02 | Spinel | ↑ | 15 | 11 (b)[6] |
| 15 | ↑ | ↑ | 0.5 | ↑ | ↑ | 15 | ↑ [6] |
| *IV | ↑ | — | — | Spinel | CeO$_2$ | 15 | |

*: Comparative samples
[1] This amount represents the ratio of noble metal/metal oxide (In Nos. B3 and B13, Pt 80-90 wt %, Rh 10-20%)
[2] This amount represents the ratio of OSC/metal oxide, OSC being in terms of metal element (Ce)
[3] spinel: MgO—Al$_2$O$_3$
[4] Oxygen sensor produced according to an example of JP patent Kokai No. 62-245148
[5] Sample Nos. B4, B5, B10, B11, B14 and B15 were produced by forming the 2nd protective layer through Step 11 (a) (flame-spraying spinel), whereas the remainders were through Step 11 (b) (coating followed by baking).
[6] Sample Nos. B14 and B15 are of the plate type.

In TEST B (1), as may be seen from FIG. 14, the Comparative Sample BI (having the first protective layer of spinel) and the Comparative Sample BIV (the first protective layer carrying noble metal) exhibits output characteristics in which the electromotive force is lowered very gradually in the vicinity of $\lambda=1$. Hence the Comparative Samples B1 and BIV are extremely low in $\lambda=1$ detection characteristics. Conversely, the Sample Nos. B1 to 15 and Comparative Samples BiII and III exhibit output characteristics which are acutely lowered in the vicinity of $\lambda=1$. Hence, these samples are superior in detective characteristics of the theoretical value ($\lambda=1$).

In TEST B (2), as will be seen from FIG. 15, the Comparative Sample BI, containing the first protective layer of spinel, has a high response frequency Hz, however, it delineates as asymmetrical response curve exhibiting fast rising and retarded decay characteristics. Therefore, these asymmetricities need to be compensated by a computer. On the other hand, the Comparative Sample BII, which is an oxygen sensor prepared in accordance with the Example disclosed in the JP Patent KOKAI Publication 62-245148 and provided with a second protective layer comprising CeO$_2$ and Pt, while exhibiting a symmetrical response curve, has an extremely low response frequency Hz. Thus the number of times (i.e., frequency) of feedback to the engine system, that is, the number of exhaust gas corrections is reduced. Thus the control width is increased and accordingly, there is a fear that the exhaust gas concentration becomes too high beyond the acceptable catalytic capacity of the ternary catalyst system. In contrast thereto, the Sample Nos. B1 to 15 and the Comparative Samples BIII and IV exhibit a symmetrical response curve, a higher response frequency and a broader amplitude, so that they are superior in the response properties.

In TEST B (3), as may be seen from FIG. 16, the aforementioned Comparative Sample BI and the Comparative Sample BIII, that is an oxygen sensor provided only with a first protective layer carrying the Pt catalyst, are subject to rich excursion, according to which deviation greatly occurs towards the rich side with respect to the excess air ratio ($\lambda$) curve by response delay when the A/F ratio (thus $\lambda$) is transiently (momentally) shifted towards the lean side ($\lambda=1.1$), even if the $\lambda$ reverts to a substantially theoretical value ($\lambda=0.98$). Conversely, with the Example Nos. B1 to 15 and the Comparative Examples BII and IV, oxygen is occluded by OSC when the air quantity is increased (on the lean side), thereby retarding the timing of outputting the lean signal and shortening the time interval of outputting the lean signal. Hence, the above described phenomenon of the rich excursion is not produced, but the $\lambda$ (also A/F ratio) reverts quickly to close to the theoretical value upon termination of the increase of the air quantity.

Thus the Samples Nos. B1 to 15 exhibit superior $\lambda=1$ detection properties and sufficient response characteristics under steady operating states. Therefore, these Samples are highly useful in an air-to-fuel ratio control system of the exhaust gas with high gas flow rate properties. In addition, $\lambda$-point deviations are not caused upon acute increase of air quantity during acceleration to provide accurate air-to-fuel ratio control. Accordingly, high purification characteristics for toxic substances may be maintained without departing from the range of the ternary catalyst system of the exhaust gas purification system.

EXAMPLE C-1 (relating to 5th and 6th Aspects, perticularly)

Figure 19:
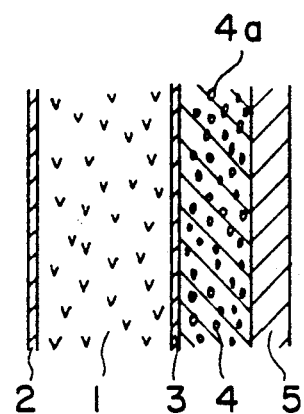
FIG. 19 is a further schematic cross section of portion II in FIG. 1.
Figure 20:
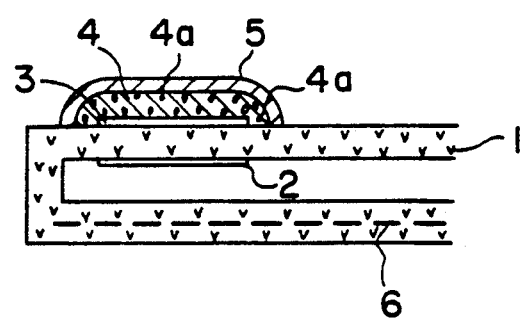
FIG. 20 is a cross section of an embodiment of the plate type sensor according to the 5th Aspect.

U-shaped tube type oxygen sensors (Sample Nos. C1 to 5 and comparative Samples CI and CII), as shown in FIGS. 1 and 19 were prepared by the following steps. The concrete composition of each sample is shown in Table 3.

Steps 1 to 9:
Same as steps 1 to 9 of Examples A.

Step 10:
Cerium nitrate was dissolved in an aqueous solution of nitric acid and its concentration was adjusted so that 2 wt % of cerium nitrate was affixed to the main body of the first protective layer of spinel.

Step 11:
The protective layer of the element produced in steps 1 to 9 were dipped in a solution obtained in step 10, as shown in FIG. 6, and were allowed to stand for about 10 minutes under a reduced pressure of 13.3 kPa (100 mHg) for impregnating the first protective layer with cerium nitrate. The element was then heat treated in atmosphere at about 700° C. as that cerium oxide was supported by the first protective layer.

Step 12: (paste for second protective layer)
Powders of Al$_2$O$_3$ having an average particle size of 0.5 μm and a purity of 99% (Sample Nos. C1 and 2) or powders of $TiO_2$ having an average particle size of 0.3 μm and a purity of 99% (Sample Nos. C3 and 4) were added to in an amount of 15 and 20 wt %, respectively, of an organic binder, and the resulting mixtures were processed into pastes by adding butyl carbitol.

Step 13: (formation of second protective layer)

(a) The first protective layer was immersed in a paste obtained in step 12 for paste coating, followed by heat treating at 600° C. in air.

(b) A spinel layer was again formed on sample No. C5 by plasma spraying.

Steps 14 to 17:
Same as steps 12 to 15 of Example C1.

EXAMPLE C-2

Figure 4B:
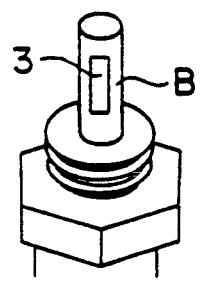
Figure 5:
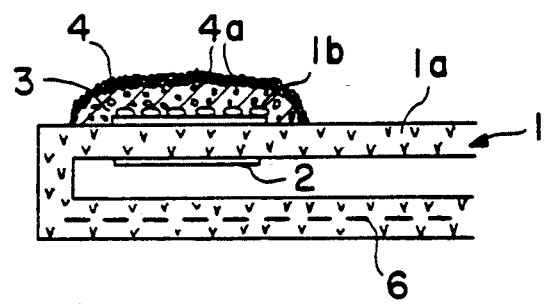
FIG. 5 is a partially enlarged cross-sectional view of the plate-like oxygen sensor shown in FIG. 4 (a)

Plate-shaped oxygen sensors as shown in FIGS. 4 (a) and 20 (Sample Nos. C6 and C7 and Comparative Sample CIII) were prepared by the following steps.

Steps 1 to 8:
Same as step 1 to 8 of Example B-2.

Step 9:
The element obtained in step 8 was immersed in a cerium nitrate solution similar to that of step 10 of Example C-1 for impregnating the element with cerium nitrate in the same way as in step 11 of Example C-1 for supporting cerium oxide in the first protective layer.

Step 10: (formation of the second protective layer)
Similarly to the step 13 of Example C-1, a spinel layer was formed by plasma spraying to a thickness of 20 μm. Similarly to the steps 12 and 13 of Example C-1, a $TiO_2$ layer was formed by paste coating (Sample C7).

Step 11:
A pair of supporting members 14 were attached by glass seals to both sides of the produced element as shown in FIG. 18.

Steps 12 to 15: (assembling to the Sensor)
Same as steps 12 to 15 of Example C-1.

EXAMPLE C-3

Figure 11A:
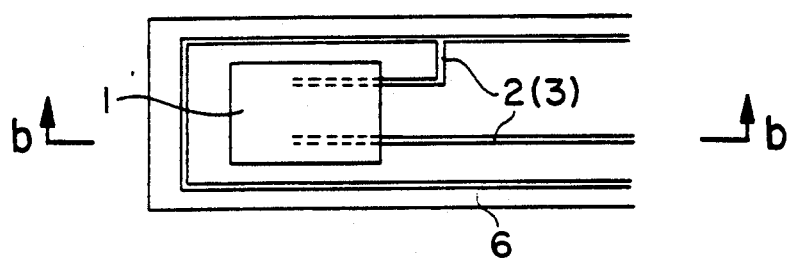
FIG. 11(a) is a top plan view (omitting the protective layer)
Figure 11B:
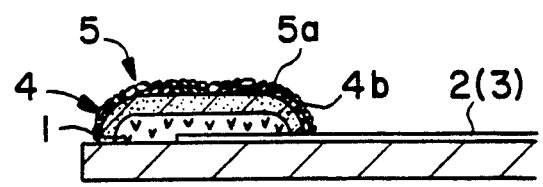
FIG. 11(b) is a cross sectional view along the b—b line in FIG. 11(a)
Figure 12:
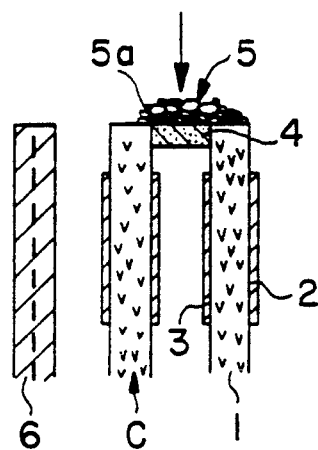
FIG. 12 is a cross sectional view of an embodiment for controlling the full range air-fuel ratio according to the 3rd Aspect (with a pumping cell element)

By the following steps, semiconductor type oxygen sensors (Sample Nos. C8 and C9, Comparative Sample CIV) shown in FIGS. 11 (a) and 21 were prepared.

Step 1:
90 wt % of $Al_2O_3$ having a purity of not less than 99%, 3 wt % of MgO, 2 wt % of CaO and 5 wt % of $SiO_2$ were mixed together and thereto was added an organic binder and a solvent, and a green sheet 0.8 mm thick was prepared by the doctor blade method.

Step 2:
Using a Pt paste, a heater pattern and an electrode shown in FIG. 11 (a) were screen printed on one surface of a green sheet to a thickness of 30 μm.

Figure 21:
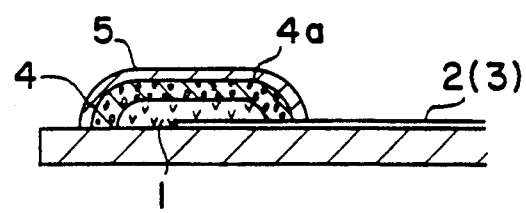
FIG. 21 is a cross section of an embodiment of a semiconductor type sensor under the 5th Aspect.
Figure 22:
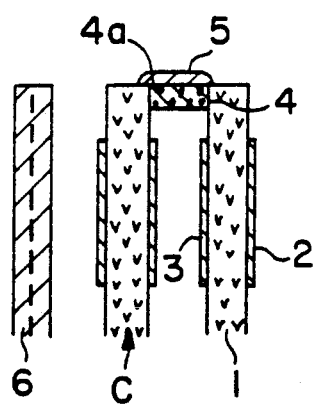
FIG. 22 is a cross sectional view of an embodiment for controlling the full range air-fuel ratio according to the 5th Aspect (with pumping cell element)

Step 3:
A green sheet 250 μm thick was prepared in the same way as in step 1, and an opening was formed at the electrode portion followed by lamination as shown in FIG. 21.

Step 4:
After removing the resin, sintering was performed at 1500° C. for 2 hours.

Step 5:
$TiO_2$ having a purity of 99.9% was dipped in a $H_2PtCl_6$ solution so that Pt accounts for 1 mole % in $TiO_2$. Drying was made under boiling.

Step 6:
After drying at 200° C. for 24 hours, heat treatment was performed in a Pt crucible in a non-oxidizing atmosphere at 1000° C.

Step 7:
After addition of Pt black powders so that the Pt accounts for 5 mole % base on $TiO_2$, followed by addition of an organic binder and a solvent to form a paste.

Step 8:
The paste obtained at steps 5 to 7 was injected into the opening formed in the laminated produced by the steps 1 to 4 to form a layer 200 μm thick. Heat treatment was performed in a reducing atmosphere of 800° C.

Step 9:
After laminating $MgO.Al_2O_3$ spinel to a thickness of 50 μm with plasma spraying to form a first protective layer, the laminate was dipped in a cerium nitrate solution prepared in the same way as at step 10 of Example C-1 for impregnation under a reduced pressure of 6.7 to 13.3 kPa (50 to 100 mmHg). The impregnated product was calcined in air at about 700° C. for supporting cerium oxide by the first protective layer.

Step 10: (formation of second protective layer)
A spinel layers 10 to 30 μm thick was formed by plasmar spraying of a spinel such as $Al_2O_3.MgO$. Steps 11 to 14: (assembling to the sensor)
Same as steps 12 to 15 of Example A.

Comparative Examples

Comparative samples Nos. CI to CIII are $ZrO_2$ solid electrolyte type oxygen sensors. The comparative samples Nos. CI and CII are U-tube shaped, while the comparative sample CIII is plate-shaped. The Comparative Sample CIV is a $TiO_2$ semiconductor type oxygen sensor.

Comparative Sample CI:
This sample is an oxygen sensor prepared in substantially the same way as in the example disclosed in the JP Patent KOKAI Publication 61-79155 (1986). After forming a first protective layer of spinel, a mixed powder slurry containing 70 wt % of $Al_2O_3$ and 30 wt % of $CeO_2$ was coated thereon, without dipping in a Ce salt solution, for substantially incorporate $CeO_2$ in the second protective layer.

Comparative Sample CII:
A mixed powder slurry containing 70 wt % of spinel and 30 wt % of $CeO_2$ was coated to form a first protective layer 50 μm thick and a second protective layer of spinel was applied by flame spraying to form a second protective layer 30 μm thick.

Comparative Sample CIII:
A mixture of powders of 70 wt % of $Al_2O_3$ and 30 wt % of $CeO_2$ was made to paste and printed, followed by co-sintering to form only a first protective layer 50 μm thick.

Comparative Sample CIV:
A spinel layer was formed to a thickness of 50 μm by flame spraying and dipped in a cerium nitrite solution to be supported in the spinel layer. (The second protective layer is not provided.)

TESTS
The following tests were conducted on the thus prepared samples.

TEST C (1):
An actual vehicle was used and the engine was run at 3000 rpm while a Si-containing oil or a (Ca+P) containing oil was injected for about 30 minutes from the regular attachment position of the oxygen sensor at a rate of 5 cc per hour. Each sample was attached to an exhaust tube at a position 30 cm downstream of the oil injecting position.

Then, as shown in FIG. 23, switching from $\lambda \approx 0.98$ to $\lambda = 1.1$ was made to shift the exhaust gas condition to the lean side, upon which time the sensor output state was investigated. The results were evaluated by the following marks:

Substantially No Output Change: A
Change of about 100 mV: B
Change of 200 mV or more: x

TEST C (2):

Each sample was put to a durability test for 200 hours on an actual car between a state of idle running for 20 minutes and a state of an A/F ratio of 12 at a gas temperature of 850° C. or higher.

The $\lambda$ (excess air ratio) value was then switched as in TEST C (1) to investigate the sensor output state.

The results are shown in the following Table 3 and FIG. 23.

layer of spinel) suffered crack formation partially. Conversely, with samples C1 to 9, such peeling or crack formation were not observed and the first and second protective layers were maintained stably fixed to the main body of the sensor element to protect the main body of the sensor element and the electrode. The sensor element exhibited excellent durability under the conditions of severe operating cycles and the phenomenon of rich excursion does not occur even after use under these conditions for a prolonged period of time, although such phenomenon was slightly observed in case with the sample C3.

Thus the samples C1 to 9 of the inventive Examples, above all the samples C1, C2 and C4 to 9, are not poisoned by Si, Ca or P, nor subjected to peeling off even under severe operating cycles to exhibit the function proper to the OSC ($CeO_2$ etc.) of stably occluding and

TABLE 3

| Sample No. C | 1st protective layer | | | 2nd protective layer | | TESTS | | | |
|---|---|---|---|---|---|---|---|---|---|
| | Metal oxide | OSC | Carrying method | Metal oxide | Thickness ($\mu$m) | C (1) $Si^{2)}$ | Ca. P | C (2) | Remarks |
| 1 | Spinel[1] | $CeO_2$ | $Ce(NO_3)_3$ immersed | $Al_2O_3$ | 30 | A | A | A | |
| 2 | ↑ | ↑ | ↑ | ↑ | 60 | A | A | A | |
| 3 | ↑ | ↑ | ↑ | $TiO_2$ | 10 | A | A | A B | |
| 4 | ↑ | ↑ | ↑ | ↑ | 50 | A | A | A | |
| 5 | ↑ | ↑ | ↑ | spinel | 30 | A | A | A | |
| 6 | $Al_2O_3$ | ↑ | ↑ | ↑ | 20 | A | A | A | |
| 7 | ↑ | ↑ | ↑ | $TiO_2$ | 20 | A | A | A | |
| 8 | spinel | ↑ | ↑ | spinel | 10 | A | A | A | |
| 9 | ↑ | ↑ | ↑ | ↑ | 30 | A | A | A | |
| *I | ↑ | — | — | $Al_2O_3$ (+ $CeO_2$) | 30 | X | B | B | 2nd P/L** partly peeled |
| *II | ↑ | $CeO_2$ | slurry coated | spinel | 30 | A | A | X | 1st P/L** peeled |
| *III | $Al_2O_3$ | ↑ | paste printed | — | — | B X | X | X | 1st P/L peeled |
| *IV | spinel | ↑ | $Ce(NO_3)_3$ immersed | — | — | X | X | B | partial cracks in spinel layer |

*: Comparative sample
**: P/L = Protective layer
[1] spinel: $MgO-Al_2O_3$
[2] "Si" at TEST C (1) represents the case where testing was made during injecting Si-contaning oil, whereas "Ca. P" represents the case where testing was made during injecting Ca and P-containing oil.

As may be seen from Table 3 and FIG. 23, when the excess air ratio $\lambda$ (or A/F ratio) shifts transiently from near the theoretical value ($\lambda = 0.98$) to the lean side ($\lambda = 1.1$), the Comparative Samples CI, CIII and CIV are subjected to rich excursion, that is, considerable deviation to the rich side of the A/F curve due to response delay, even when the $\lambda$ (or A/F ratio) returns to substantially the theoretical value ($\lambda = 0.98$). In contrast thereto, with the Samples Nos. C1 to 9 of the inventive Examples and the Comparative Sample CII, oxygen is stored (occluded) at the time of increased air quantity due to the presence of the OSC to retard the timing of outputting of the lean signal to shorten the period of time during which the lean signal is outputted. Thus the above mentioned phenomenon of the rich excursion does not occur, but the $\lambda$ (or A/F ratio) reverts quickly to near the theoretical value upon termination of the increasing of the air quantity.

In TEST C (2), peeling occurred with the Comparative Samples CII and CIII at the first protective layer or the protective layer (consisting only of the first protective layer). Thus the rich excursion occurred after termination of the durability test. As for the Comparative Sample C1, the second protective layer was peeled off partially. As for the Comparative Sample CIV, the protective layer (consisting only of the first protective releasing oxygen at the time of acute air quantity increase during acceleration. Accordingly, the purification characteristics of toxic substances may be maintained at a high level without deviating from the suitable range (so-called window) of the ternary catalyst system for the exhaust gas purification system.

It should be noted that modification may be made in the art without departing from the gist and scope of the present invention as disclosed and claimed as annexed hereinbelow.

What is claimed is:

1. A method of producing an oxygen sensor for air-fuel ratio control comprising a sensor element having a main body and electrodes disposed on sides of the main body and a protective layer covering the electrode on the side of the sensor element assigned to be exposed to a gas to be measured for oxygen, the method comprising the steps of:

(a) disposing electrodes on sides of the main body,
    (b) applying spherical particles made of a material from which the main body of the sensor element is made at a portion of the main body at least corresponding to a position where the electrode to be exposed to the gas is disposed, (c) forming said protective layer on the spherical particles applied to said portion of the main body, said protective layer being comprised of metal oxide and having a length, and (d) immersing at least a portion of said protective layer in a metal salt of an oxygen storage component.

2. The method as defined in claim 1, in which the oxygen storage component is impregnated by immersion in an amount of 0.2–8 wt % in terms of metal element of oxygen storage component relative to the heat-resistant metal oxide of the protective layer.

3. The method as defined in claim 1 further comprising the step of treating said immersed portion of said protective layer by heating said immersed portion of said protective layer at 300°–850° C. in an oxidizing atmosphere.

4. The method as defined in claim 2, in which 50–95% of said length of said protective layer is immersed in said metal salt of said oxygen storage component.

5. The method as defined in claim 1, wherein said step of applying said spherical particles forms a spherically protruded portion by applying said spherical particles with an average size of 40–100 μm.

6. The method as defined in claim 1, in which a spherically protruded portion is formed by co-sintering the main body of the sensor element and the spherical particles applied to the surface of the main body.

7. The method as defined in claim 1, in which a spherically protruded portion is formed by first depositing the electrode on the main body of the sensor element at the position where the electrode is to be exposed to the gas, and then applying said spherical particles having an average particle size of 40–100 μm.

8. The method as defined in claim 1, in which the protective layer is formed by plasma-spraying said metal oxide material.

9. The method as defined in claim 1, in which the protective layer is formed by printing said metal oxide material on a green sheet of sensor element main body material followed by co-sintering the green sheet and the printed metal oxide material.

10. The method as defined in claim 1, in which the metal salt of the oxygen storage component is a nitrate and/or acetate.

11. The method as defined in claim 1, in which the immersion is carried out at a pH of 5 or less at room or higher temperature.

12. The method as defined in claim 1, in which the oxygen storage component is selected from the group consisting of oxides of Ce and V and mixtures thereof.

13. A method of producing an oxygen sensor for air-fuel ratio control comprising a sensor element having a main body and electrodes disposed on sides of the main body and protective layers on the side of the sensor element assigned to be exposed to a gas to be measured for oxygen, the method comprising the steps of:

(a) disposing electrodes on sides of the main body, (b) forming a first protective layer of metal oxide on said side of the sensor element, (c) immersing the first protective layer in a solution of a salt of a noble metal, and (d) coating a slurry of metal oxide and oxygen storage component on said first protective layer to provide a second protective layer.

14. The method as defined in claim 13, in which the slurry is prepared by impregnating a powder of the heat-resistant metal oxide with a metal salt of the oxygen storage component.

15. The method as defined in claim 13, in which an ingredient of the slurry for the heat-resistant metal oxide is a compound which provides metal oxide through thermal decomposition.

16. The method as defined in claim 13, in which powders in the slurry for forming the second protective layer have an average particle size of not more than 2 μm.

17. The method as defined in claim 13, further comprising a step after said coating of the slurry of subjecting the sensor element to heating at 600°–900° C. to form the second protective layer.

18. A method of producing an oxygen sensor for air-fuel ratio control comprising a sensor element having a main body and electrodes disposed on sides of the main body and protective layers on the side of the sensor element assigned to be exposed to a gas to be measured for oxygen, the method comprising the steps of:

(a) disposing electrodes on sides of the main body, (b) forming a first protective layer of metal oxide on said side of the sensor element, (c) immersing the first protective layer in a solution of a salt of a noble metal, (d) forming a second protective layer of metal oxide on said first protective layer, and (e) immersing the second protective layer in a solution of a metal salt of an oxygen storage component.

19. The method as defined in claim 18, in which the first protective layer is formed by plasma-spraying said metal oxide.

20. The method as defined in claim 18, in which the first protective layer is formed by applying metal oxide on a green body of sensor element material and is co-sintered with the sensor element.

21. The method as defined in claim 18, in which the salt of said noble metal contained in the solution comprises $H_2PtCl_6$ and the solution contains a Pt ion concentration of 0.01–5 g/l.

22. The method as defined in claim 18, in which the second protective layer is formed by at least one of plasma-spraying metal oxide and coating with finely powdered metal oxide.

23. The method as defined in claim 22, in which the fine powder has an average particle size of not more than 1 μm.

24. The method as defined in claim 18, in which the metal salt of the oxygen storage component is selected from the group consisting of salts of nitric and acetic acid.

25. The method as defined in claim 18, in which the solution of the oxygen storage component metal salt has a pH of 5 or less and the immersion is carried out at room or higher temperature.

26. The method as defined in claim 18, in which the second protective layer is immersed not more than 95% of its entire length.

27. The method as defined in claim 18, in which the immersion of the second protective layer is conducted so as to impregnate the oxygen storage component in the second protective layer in an amount of 0.2–8 wt % of a weight of the metal oxide of the second protective layer.

28. The method as defined in claim 18, in which after the immersion to form the second protective layer, the second protective layer is subjected to heat treatment in an oxidizing atmosphere at 300°-850° C.

29. A method of producing an oxygen sensor for air-fuel ratio control comprising a sensor element having a main body and electrodes disposed on sides of the main body and protective layers on the side of the sensor element assigned to be exposed to a gas to be measured for oxygen, the method comprising the steps of:
   (a) disposing electrodes on sides of the main body,
   (b) forming a first protective layer of metal oxide on said side of the sensor element, said first protective layer having a length,
   (c) immersing at least a portion of the first protective layer in a metal salt solution of an oxygen storage component, and
   (d) forming a second protective layer of a metal oxide on said first protective layer.

30. The method as defined in claim 29, in which the formation of the heat-resistant metal oxide layer for either of the first and second protective layers is carried out by flame spraying.

31. The method as defined in claim 29, in which the first protective layer of metal oxide is formed by co-firing a green sheet of sensor element main body material with a green coating layer of metal oxide applied on the green sheet.

32. The method as defined in claim 29, in which the second protective layer is formed by coating the first protective layer with a metal oxide paste and then baking it.

33. The method as defined in claim 29, in which after the immersion in the oxygen storage component metal salt solution, the first protective layer is heat treated in an oxidizing atmosphere at 300°-860° C.

34. The method as defined in claim 29, in which the oxygen storage component is impregnated by the immersion of the first protective layer in an amount of 0.2-8% of a weight of the metal oxide of the first protective layer.

35. The method as defined in claim 29, in which 50-95% of said length of said first protective layer is immersed in said metal salt of said oxygen storage component.

36. The method as defined in claim 29, in which the metal salt of the oxygen storage component is selected from the group consisting of salts of nitric and acetic acid.

37. The method as defined in claim 29, in which the immersion in the oxygen storage component metal salt solution is carried out at a pH of 5 or less under a reduced or pressurized pressure at room or higher temperature.

38. The method as defined in claim 22, in which the paste of the heat-resistant metal oxide has an average particle size of 1 μm or less.

39. The method as defined in claim 29, in which the immersion in the oxygen storage component metal salt solution is carried out at a pH of 5 or less at room or higher temperature.

40. The method as defined in claim 29, in which the method further includes a step for incorporating a noble metal catalyst in the second protective layer.

* * * * *